(12) United States Patent
Brooks et al.

(10) Patent No.: US 8,932,810 B2
(45) Date of Patent: Jan. 13, 2015

(54) IDENTIFICATION OF MUTATION AND METHOD FOR DETECTING LAVENDER FOAL SYNDROME IN THE HORSE

(75) Inventors: Samantha A. Brooks, Van Etten, NY (US); Nicole Gabreski, Coudersport, PA (US); Doug Antczak, Ithaca, NY (US)

(73) Assignee: Cornell University, Ithaca, NY (US)

( * ) Notice: Subject to any disclaimer, the term of this patent is extended or adjusted under 35 U.S.C. 154(b) by 292 days.

(21) Appl. No.: 13/093,173

(22) Filed: Apr. 25, 2011

(65) Prior Publication Data

US 2011/0265193 A1 Oct. 27, 2011

Related U.S. Application Data

(60) Provisional application No. 61/343,121, filed on Apr. 23, 2010.

(51) Int. Cl.
*C07H 21/04* (2006.01)
*C12Q 1/68* (2006.01)

(52) U.S. Cl.
CPC ........ *C12Q 1/6888* (2013.01); *C12Q 2600/124* (2013.01); *C12Q 2600/156* (2013.01); *C12Q 2600/172* (2013.01)
USPC ......... 435/6.1; 435/91.1; 435/91.2; 536/23.1; 536/24.3

(58) Field of Classification Search
None
See application file for complete search history.

(56) References Cited

U.S. PATENT DOCUMENTS

2011/0023157 A1* 1/2011 Bedell et al. .................... 800/14
2013/0022972 A1* 1/2013 Guthrie et al. ............... 435/6.11

OTHER PUBLICATIONS http://risingrainbow.blogspot.com/2007/06/breeding-carriers-of-lavender-foal.html, Jun. 17, 2007.*
http://www.laboklin.co.uk/laboklin/showGeneticTest.jsp?testID=8301HGD, copyright date 2007.*
website VHL, Artnr P854 test for Lavender Foal Syndrome. 2008.*
Gabreski et al. J. of Equine Veterinary Science, vol. 29, Issue 5, pp. 321-322, May 2009.*
http://web.up.ac.za/default.asp?ipkCategoryID=11671&articleID=3268, Posted Nov. 4, 2009.*
Brooks et al. (PLoS Genetics, vol. 6, No. 4, pp. e0000909 Apr. 15, 2010).*
Genbank Accession No. HM063929, Jun. 2, 2010.*
Glaser et al. "Lavender Foal Syndrome Genetic Test" Animal Health Diagnostic Center, Aug. 26, 2010.*
Bierman et al. Animal Genetics, vol. I 41, Supple 2, pp. 199-2001, Nov. 10, 2010, online.*
http://web.archive.org/web/20120829113422/http://www.vgl.ucdavis.edu/services/horse.php, Wayback Machine Date Aug. 29, 2012.*
Illumina SNP genotypine. "Equine SNP50 Genotyping Bead Chip" Sep. 15, 2008.*
Bowling AT (1996) Medical Genetics. Horse Genetics. Wallingford, UK: CABI International. pp. 105-106.
Brooks SA. et al., (2010) PLoS Genet. Apr. 15; Whole-genome SNP association in the horse: identification of a deletion in myosin Va responsible for Lavender Foal Syndrome.
Fanelli HH (2005) Coat colour dilution lethal ('lavender foal syndrome'): a tetany syndrome of Arabian foals. Equine Veterinary Education 17: 260-263.
Page et al. (2006) Clinical, clinicopathologic, postmortem examination findings and familial history of 3 Arabians with lavender foal syndrome. J Vet Intern Med 20: 1491-1494.

* cited by examiner

*Primary Examiner* — Jeanine A Goldberg
(74) *Attorney, Agent, or Firm* — Hodgson Russ LLP

(57) ABSTRACT

Provided is a method for determining whether a horse is normal, a carrier, or is affected with Lavender Foal Syndrome (LFS). The method entails, in a biological sample obtained or derived from a horse, determining a single nucleotide deletion which introduces a translational stop codon in the 49$^{th}$ codon of exon 30 of the equine MYO5A gene. Homozygosity for the absence of the deletion is indicative that the horse is normal for LFS. Heterozygosity for the deletion is indicative that the horse is a carrier of LFS. Homozygosity for the deletion is indicative that the horse is affected with LFS. Methods for selecting horses for breeding and kits for determining the LFS-associated deletion are also provided.

10 Claims, 1 Drawing Sheet

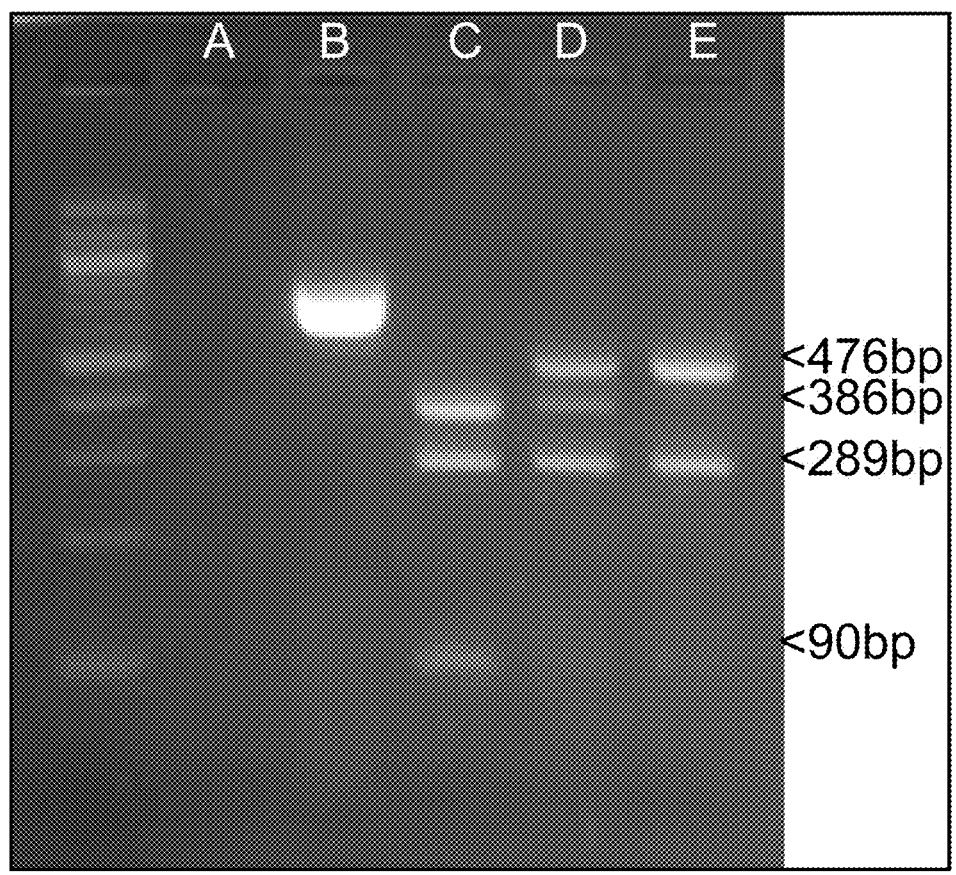

… (1) …

IDENTIFICATION OF MUTATION AND METHOD FOR DETECTING LAVENDER FOAL SYNDROME IN THE HORSE

This application claims priority to U.S. Provisional Patent Application No. 61/343,121, filed on Apr. 23, 2010, the disclosure of which is incorporated herein by reference.

FIELD OF THE INVENTION

The present invention relates generally to genetic disease in horses and more particularly to diagnosis of the horse disease referred to as Lavender Foal Syndrome.

BACKGROUND OF THE INVENTION

Heritable disorders affect many domestic species, including the horse. In the Arabian breed of horse a neurological disorder has been reported that is lethal soon after birth [Bowling A T (1996) Medical Genetics. Horse Genetics. Wallingford, UK: CABI International. pp. 105-106]. Affected foals can display an array of neurological signs including tetanic-like seizures, opisthotonus, stiff or paddling leg movements and nystagmus [Fanelli H H (2005) Coat colour dilution lethal ('lavender foal syndrome'): a tetany syndrome of Arabian foals. Equine Veterinary Education 17: 260-263.]. Mild leucopenia is sometimes observed [Fanelli H H (2005), and Page P, Parker R, Harper C, Guthrie A, Neser J (2006) Clinical, clinicopathologic, postmortem examination findings and familial history of 3 Arabians with lavender foal syndrome. J Vet Intern Med 20: 1491-1494]. These neurologic impairments prevent the foal from standing and nursing normally and, if not lethal on their own, are often cause for euthanasia. In addition to these abnormalities, affected foals possess a characteristic diluted "lavender" coat color. This resulting coat color, variously described as pale gray, pewter, and light chestnut, as well as lavender, has coined the name "Lavender Foal Syndrome" (LFS) [Fanelli H H (2005)]. Also called "Coat Color Dilution Lethal" [Fanelli H H (2005)]. There is currently no treatment for LFS available. Additionally, initial diagnosis can be difficult as the clinical signs of LFS can easily be confused with a number of neonatal conditions including neonatal maladjustment syndrome and encephalitis [Fanelli H H (2005)]. Thus, there is an ongoing and unmet need provide improved methods for diagnosis of LFS. The present invention meets this and other needs.

SUMMARY OF THE INVENTION

The present invention provides a method for determining whether a horse is normal, is a carrier of, or is affected with developing Lavender Foal Syndrome (LFS).

The method comprises, in a biological sample obtained or derived from a horse, determining the presence or absence of a single nucleotide deletion that introduces a stop codon in exon 30 of the equine MYO5A gene. In one embodiment, the deletion is a deletion of the nucleotide in position 147 of SEQ ID NO:1, which represents exon 30 of the equine MYO5A gene. An exon 30 nucleotide sequence comprising a deletion of the $147^{th}$ nucleotide is presented in SEQ ID NO:2. The deletion of the $147^{th}$ nucleotide in exon 30 of the equine MYO5A gene introduces a translational reading frame change, which results in a stop codon at the $49^{th}$ codon of this exon. The genome of any particular horse can contain this mutation on one or both chromosome homologues where the MYO5A gene is located (equine chromosome 1). Genetically normal horses are considered those in which both alleles do not have the deletion. Affected horses are those in which both alleles contain the deletion. Carrier horses are those in which only one allele has the deletion.

The presence or absence of the deletion can be determined using any suitable technique, including nucleic acid and protein analysis. For example, the deletion can be determined by analysis of DNA or RNA polynucleotides. The polynucleotides can be analyzed directly, or they can be amplified and the amplified polynucleotides can be analyzed. Suitable methods for determining the presence or absence of the mutation in polynucleotides include but are not necessarily limited to polynucleotide sequencing, restriction fragment length polymorphism mapping, and any of various hybridization techniques that are capable of determining a single base mismatch between polynucleotides, and/or amplification methods, such as by polymerase chain reaction (PCR), reverse-transcriptase PCR, real-time PCR, and the like. It is also feasible to determine the presence or absence of the deletion by determining truncated protein encoded by a MYO5A gene that contains the deletion. In one embodiment, a determination of the presence of a truncated protein encoded by a MYO5A gene that contains the deletion can be used to determine that the deletion is present, and therefore for identification of the horse as not normal with respect to LFS status.

The invention also provides isolated nucleic acid molecules that comprise the deletion and kits for determining whether or not the deletion is present.

The invention also includes a method for selecting horses for breeding. The method comprises testing a biological sample obtained or derived from a horse to detect the deletion in one or both alleles, and eliminating horses with the deletion from a breeding stock, or breeding horses with the deletion with genetically normal horses. The invention also includes receiving the LFS deletion status of a horse and selecting a horse for breeding (or not breeding) based at least in part on the LFS deletion status.

The invention can be carried out using any suitable biological sample obtained from a horse that would be expected to contain chromosomal DNA and/or mRNA or protein encoded by the horse genome. In one embodiment, the horse is an Arabian breed of horse. In one embodiment, the Arabian horse is an Egyptian Arabian horse.

BRIEF DESCRIPTION OF THE FIGURE

FIG. 1 provides a photographic representation of electrophoretic separation of samples of horse DNA that have been subjected to restriction fragment length polymorphism mapping for the LFS-associated deletion.

DETAILED DESCRIPTION OF THE INVENTION

The present invention provides a method for determining whether a horse is normal, is a carrier of, or is affected with (or is predisposed to developing) Lavender Foal Syndrome (LFS). The method comprises, in a biological sample obtained or derived from a horse, determining the presence or absence of a deletion of a particular nucleotide in the equine MYO5A gene which is located on equine chromosome 1. According to the invention, genetically normal horses are considered those which do not have the deletion (homozygous for the absence of the deletion). Affected horses are those in which both chromosomes contain the deletion (homozygous for the deletion). Carrier horses are those in which only one chromosome contains the deletion (heterozygous for the deletion). The deletion alters the putative amino acid sequence of the protein encoded by the equine MYO5A gene, which is believed to contain at least 39 exons. In particular, the deletion alters the main MYO5A gene reading frame beginning at the 49$^{th}$ amino acid of exon 30 and introduces a stop codon at the 61$^{st}$ codon of exon 30. The introduction of this stop codon may result in premature termination of transcription, and in any event results in an open reading frame which codes for a protein that is 379 amino acids shorter at the C-terminus of the protein, relative to the protein encoded by the equine MYO5A gene that does not contain the deletion. Thus, in one embodiment, the invention includes detecting the presence of the deletion by determining a polynucleotide sequence from a biological sample obtained or derived from a horse, wherein the polynucleotide encodes an amino acid sequence encoded by exon 30 of the equine MYO5A gene which differs from the normal amino acid sequence, wherein this difference begins at the 49$^{th}$ amino acid of exon 30, and includes a stop codon at the 61$^{st}$ codon of exon 30. Likewise, in one embodiment, the invention includes detecting the absence of the deletion by determining a polynucleotide sequence from a biological sample obtained or derived from a horse, wherein the polynucleotide encodes an amino acid sequence encoded by exon 30 of the equine MYO5A which does not comprise the LFS-associated deletion.

Determining the presence or absence of the LFS-associated deletion can be performed using any suitable techniques, reagents and compositions. Accordingly, the invention includes but is not necessarily limited to detecting the presence or absence of the deletion by direct analysis of RNA or DNA, by analysis of polynucleotides amplified from RNA or DNA, or by analysis of protein encoded by an equine MYO5A gene that does or does not comprise the deletion, and any combination(s) thereof. Those skilled in the art will recognize that any technique now known or hereafter developed for detecting the presence or absence of the deletion can be used to perform the method of the invention. In this regard, all nucleotide sequences presented herein include DNA and RNA equivalents thereof, as the case may be, and also include complementary sequences. Further, all nucleotide sequences encoding amino acid sequences presented herein can be used in performance of the invention.

The deletion determined by the method of the invention is in one embodiment a deletion of the nucleotide in position 147 of SEQ ID NO:1. SEQ ID NO:1 represents exon 30 of the equine MYO5A gene. This exon is located on horse chromosome 1 at chr1:138235569-138235769 using nucleotide numbering provided in the September 2007 Equus caballus draft assembly EquCab2, which is a publically accessible database. The sequence of exon 30 comprising a deletion of the 147$^{th}$ nucleotide is presented in SEQ ID NO:2.

SEQ ID NO:1 is:
GGCTCCTGGAATCCCAGCTCCAGTCGCA-
GAAGAGGAGCCATGAGAATGAGGCTGAA GCCCTC-
CGCGGGGAGATCCAGAGCCTGAAGGAG-
GAGAACAACCGGCAGCAGCAGC
TGCTGGCCCAGAACCTGCAGCTGC-
CCCCAGAGGCCCGCATCGAGGCCAGCCTGCAG
CATGAGATCACCCGGCTGACCAACGAAAACTTGG.
The 147$^{th}$ nucleotide that is deleted in the LFS-associated deletion is shown in bold and enlarged in SEQ ID NO:1. The invention includes detecting the absence of the deletion in the RNA equivalent of this SEQ ID NO:1.

SEQ ID NO:2 is:
GGCTCCTGGAATCCCAGCTCCAGTCGCA-
GAAGAGGAGCCATGAGAATGAGGCTGAA GCCCTC-
CGCGGGGAGATCCAGAGCCTGAAGGAG-
GAGAACAACCGGCAGCAGCAGC
TGCTGGCCCAGAACCTGCAGCTGC-
CCCCAGAGGCCGCATCGAGGCCAGCCTGCAG CAT-
GAGATCACCCGGCTGACCAACGAAAACTTGG. The juxtaposed C and G (nucleotides 146 and 148 of SEQ ID NO:1) due to the deletion of the C at the 147$^{th}$ position of SEQ ID NO:1 are shown in bold and enlarged font. The invention includes detecting the presence of the deletion in the RNA equivalent of this SEQ ID NO:2.

In various embodiments, a horse can be identified as normal for LFS by determining that the horse is homozygous for SEQ ID NO:1. A horse can be identified as a carrier of LFS by determining heterozygous alleles for exon 30, wherein one allele comprises SEQ ID NO:1 and the other allele comprises SEQ ID NO:2. A horse can be identified as affected or predisposed to LFS by determining homozygous alleles for SEQ ID NO:2. Those skilled in the art will recognize that, due to the redundancy of the genetic code, certain horses may have exon 30 sequences which differ from the nucleotide sequences presented herein, but such exon 30 sequences will not change the amino acid sequences encoded by SEQ ID NO:1 or SEQ ID NO:2. Such exon sequences can be readily envisaged by those skilled in the art. Further, determining the presence or absence of a deletion in any such exon sequence that introduces a translational stop signal at the 49$^{th}$ codon of exon 30 in the equine MYO5A gene are encompassed within the scope of this invention. Thus, determining all nucleic acid sequences that encode the amino acid sequences set forth in SEQ ID NO:3 and SEQ ID NO:4 are included within the scope of the invention.

Suitable techniques for determining the presence or absence of the deletion in nucleic acids obtained or derived from horses include but are not limited to restriction fragment length polymorphism (RFLP) mapping, amplification reactions, hybridization of nucleic acids to allele-specific probes or oligonucleotide arrays, by using various chip technologies, by polynucleotide sequencing techniques, and combinations thereof. The nucleic acids may be used directly or may be amplified enzymatically in vitro by, for example, use of the polymerase chain reaction (PCR) or any other in vitro amplification methods. For amplification and/or sequencing reactions, and for including in kits provided by the invention, primers can be designed which hybridize to a target sequence in nucleic acids obtained or derived from horses and used for sequencing or for amplification to obtain nucleic acid amplification products (amplicons) which contain the deletion site. Those skilled in the art will recognize how to design suitable primers and perform amplification reactions in order to carry out various embodiments of the invention. In general, the primers should be long enough to be useful in sequencing and/or amplification reactions, and generally primers which are at least twelve bases in length are considered suitable for such purposes. It will be readily recognized by the skilled artisan that while particular sequences of primers are provided herein, other primer sequences can be designed to detect the presence or absence of the deletion.

In one embodiment, the presence or absence of the deletion is determined using a PCR based Restriction Fragment Length Polymorphism (PCR-RFLP) assay. In one embodiment, the PCR-RFLP analysis utilizes a restriction endonuclease that recognizes a Fau I site (CATATG). In one embodiment, the presence or absence of the deletion is determined by using a PCR-RFLP assay wherein presence of the deletion abolishes a Fau I site, which results in a distinct RFLP pattern for nucleic acids which contain, and which do not contain the deletion.

In one embodiment, PCR-RFLP analysis using Fau I restriction endonuclease digestion of nucleic acids comprising only a normal equine MYO5A exon 30 sequence produces an electrophoretic separation pattern comprising two PCR-RFLP products which each have a distinct length, whereas Fau I PCR-RFLP analysis of nucleic acids comprising the equine MYO5A exon 30 sequence that contains the deletion results in a PCR-RFLP product that has a nucleotide length equivalent to the sum of the lengths of the two PCR-RFLP digestion products obtained by analysis of nucleic acids from a normal horse. Thus, in one embodiment, PCR-RFLP analysis using Fau I restriction endonuclease digestion of nucleic acids from a carrier horse will yield three products, each having a distinct length. A representative example of PCR-RFLP analysis using Fau I is presented in FIG. 1.

Representative and non-limiting primers for use in amplification of horse nucleic acids for determining the LFS-associated deletion include but are not limited to primers with the following sequences: 5'-CAG GGC CTT TGA GAA CTT TG-3' (Myo5a.Exon30.RFLP.F; (SEQ ID NO:5)) and 5'-CAG CCA TGA AAG ATG GGT TT-3' (Myo5a.Exon30.R; (SEQ ID NO:6)).

In certain embodiments, the invention provides a composition comprising an isolated horse polynucleotide and components used for nucleic acid hybridization and/or amplification and/or restriction enzyme digestions. Accordingly the compositions can additionally comprise a DNA polymerase, a reverse transcriptase, free nucleotide triphosphates, salts, buffers, restriction endonucleases, and other reagents typically employed to hybridize and/or amplify and/or analyze nucleic acids, and combinations of the foregoing. In one embodiment, the invention provides an isolated horse polynucleotide and/or a polynucleotide amplified from a horse polynucleotide, wherein the polynucleotide and/or the amplified polynucleotide is hybridized to one or more amplification or sequencing primers. The hybridized nucleic acids may be present in a buffer suitable for nucleic acid polymerization or sequencing reactions.

The invention also provides an isolated horse polynucleotide and/or a polynucleotide amplified from a horse polynucleotide wherein the polynucleotide is hybridized to at least one probe that is present in an array. The array may be present on, for example, a chip used to determine the presence or absence of a plurality of distinct polynucleotides. Such chips are commercially available and can be customized to detect the presence or absence of essentially any polynucleotide, which may be distinct from one another by a single nucleotide. The invention also provides isolated nucleic acids which comprise the equine MYO5A exon 30 sequence with and without the deletion. "Isolated" means the material has been separated from its natural environment (i.e., separated from horse tissue, horse cells, biological fluid from a horse, etc.). The isolated nucleic acids may be present, for example, in a recombinant vector, such as a plasmid, shuttle vector, or the like, or they may be isolated by, for example, extraction and separation on a separation medium, such as agarose or polyacrylamide.

The present invention also includes determining the presence or absence of the deletion by detecting all or a portion of protein that is encoded by a polynucleotide that contains the site where LFS-associated deletion occurs, or by detecting fragments of such proteins. For example, it is expected antibodies that are specific for the normal protein, and antibodies that are specific for a protein encoded by a polynucleotide that contains the LFS-associated deletion can be raised. In various embodiments, the antibodies can recognize and discriminate between such proteins based on the presence or absence of amino acid sequences that are encoded due to the presence or absence of the deletion. In this regard, SEQ ID NO:1 encodes a portion of a protein which contains the following amino acid sequence: LLESQLQSQKRSHENEAEALRGEIQSLKEENNRQQQLLAQNLQLPPEARIEASLQHEITRLTNENL (SEQ ID NO:3). Thus, identifying a protein comprising SEQ ID NO:3 in a biological sample obtained or derived from a horse is indicative that the horse is not affected with LFS, since there must be at least one allele that does not comprise the LFS-associated deletion in the sample and therefore the horse cannot be homozygous for the deletion.

SEQ ID NO:2 encodes a portion of a protein which contains the following amino acid sequence: LLESQLQSQKRSHENEAEALRGEIQSLKEENNRQQQLLAQNLQLPPEAASRPACSMRSPG (SEQ ID NO:4). This amino acid sequence differs from SEQ ID NO:3 beginning at the 49$^{th}$ amino acid, which is the location of an open reading frame shift due to the deletion of the 147$^{th}$ nucleotide in SEQ ID NO:1. In addition to the difference in amino acid sequence relative to SEQ ID NO:3, a stop codon is created after the C-terminal Gly shown in SEQ ID NO:4 (i.e., the deletion introduces a translational stop signal at the 61$^{st}$ codon of exon 30). Accordingly, identifying a protein comprising SEQ ID NO:4 in a biological sample obtained or derived from a horse is indicative that the horse is not normal with respect to LFS, since there must be at least one allele that comprises the LFS-associated deletion in the sample, and therefore the horse cannot be homozygous for the absence of the deletion.

It is expected that antibodies can be raised using standard and well recognized techniques for immunization of mammals and production of antibody-producing hybridomas from the immunizations. It is also expected that the antibodies can be raised using any of a variety of compositions that contain the particular horse protein or fragments thereof as an immunogen. The isolated and/or purified proteins or fragments thereof can be produced or isolated using any suitable technique. Further, any technique, device, system and/or reagents can be used to detect the different proteins in the biological sample. In non-limiting examples, the proteins can be detected and discriminated from one another using any immunodetection techniques, which include but are not necessarily limited to Western blot, an enzyme-linked immunosorbent assay (ELISA), or any modification of such assays that are suitable for detecting proteins of interest.

In various other embodiments, any suitable specific binders, e.g., natural or engineered ligands that bind to the horse proteins, aptamers, and small molecule binders, etc., can be used. As used herein, a "specific binder" refers to any substance that binds to target or analyte with desired affinity and/or specificity. In one embodiment, one or both specific binders are antibodies, which includes not only intact polyclonal or monoclonal antibodies, but also fragments thereof (such as Fab, Fab', F(ab')$_2$, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. The specific binders can be used in any suitable form. For example, one or both specific binders can be immobilized on a solid surface or linked to a detectable and/or be provided in physical association with a solid matrix. The solid matrix may be present in a multi-well assay plate, beads, a lateral flow device or strip, or any other form or format that is suitable for keeping the specific binders in a position whereby the proteins present in or otherwise derived from a biological sample obtained from a horse can be captured and be detected. The specific binders may be covalently or non-covalently associated with the solid matrix. The assay may be configured to provide a detectable signal indicating the presence of one or both proteins. Such immunodetection systems can be combined with suitable controls.

In various embodiments, the invention further comprises fixing in a tangible medium the determination of whether a horse is normal, a carrier or is affected with LFS. The tangible medium can be any type of tangible medium, such as any type of digital medium, including but not limited a DVD, a CD-ROM, a portable flash memory device, etc. The invention includes providing the tangible medium to a breeder to assist with one or more aspects of a breeding program.

Also provided in the present invention are kits for detecting the presence or absence of the LFS-associated deletion. The kits can comprise reagents for nucleic acid based detection of the presence or absence of the deletion, or specific binders, such as antibodies, for detecting the presence or absence of a protein that is encoded by a MYO5A polynucleotide that either comprises, or does not comprise, the LFS-associated deletion.

In one embodiment, the kits comprise reagents for extraction/preparation of nucleic acid samples and pair(s) of specific primers for use in identification of the deletion. In another embodiment, the kits provide antibodies and compositions used for probing samples with the antibodies to determine whether or not the horse genome comprises the deletion, and expresses one protein or the other accordingly.

Polynucleotide sequences for detecting the presence or absence of the LFS-associated deletion can be identical to, substantially identical to, completely complementary to, or substantially complementary to polynucleotide sequences that encode the amino acid sequence set forth in SEQ ID NO:3 or SEQ ID NO:4 The polynucleotide sequences can also be, be identical to, substantially identical to, completely complementary to, or substantially complementary to polynucleotide sequences that flank or are adjacent to the target polynucleotide sequences that encode the amino acid sequence set forth in SEQ ID NO:3 or SEQ ID NO:4. Such flanking and/or adjacent sequences can be determined from the EquCab2 database described above.

In some embodiments, the polynucleotide sequences can hybridize to polynucleotide sequences that encode the amino acid sequence set forth in SEQ ID NO:3 or SEQ ID NO:4, or MYO5A sequences that flank or are adjacent to the target polynucleotide sequences that encode the amino acid sequence set forth in SEQ ID NO:3 or SEQ ID NO:4, under low, middle or high stringent conditions. Stringency of nucleic acid hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Current Protocols in Molecular Biology (Ausubel et al. eds., Wiley Interscience Publishers, 1995); Molecular Cloning: A Laboratory Manual (J. Sambrook, E. Fritsch, T. Maniatis eds., Cold Spring Harbor Laboratory Press, 2d ed. 1989); Wood et al., *Proc. Natl. Acad. Sci. USA*, 82:1585-1588 (1985).

The invention can be carried out using any suitable biological sample obtained from a horse. A suitable biological sample is one that would be expected to contain genomic DNA, RNA, and/or protein encoded by the MYO5A gene (with and/or without the deletion). Suitable sources of biological samples include but are not limited to hair, blood, serum, plasma, mucosal scrapings, tissue biopsies, semen and saliva. In one embodiment, the biological sample is hair.

In one embodiment, the biological sample is obtained from the horse and used directly in determining the presence or absence of the deletion. In another embodiment, the biological sample is derived from a horse by obtaining a biological sample from the horse and subjecting it to a processing step before the biological sample is used in determining the presence or absence of the deletion. In some examples, the processing step can be carried out to isolate, purify and/or amplify polynucleotides or polypeptide sequence to be analyzed in determining the presence or absence of the deletion.

It is contemplated that determining the presence or absence of the LFS deletion in any horse can be achieved using the present invention. Non-limiting examples of horses for which the present invention is useful include but are not necessarily limited to Arabian breeds of horse. In one embodiment, the Arabian breed of horse is an Egyptian Arabian horse.

The present invention also provides a method for selecting horses for breeding. In this regard, prevention of the economic and emotional losses associated with lethal conditions in foals, including those affected with LFS, is a high priority, particularly among Arabian horse breeders. The market for Egyptian Arabian horses particularly values certain popular bloodlines. This leads to close breeding as owners seek to increase the percentage of this ancestry in their foal crop. This breeding strategy thus increases the need for vigilant prevention of recessive genetic disorders. The test disclosed here is expected to become a pivotal tool for breeders seeking to breed within lines segregating for LFS, yet minimize or eliminate the production of affected foals. Thus, testing for the LFS allele will be a valuable aid to breeders seeking to avoid losing foals while still using many of the popular lines that may carry LFS. As the Arabian horse was used to develop many of the modern light horse breeds it is possible that the LFS allele is present in these breeds as well, and the method disclosed herein is expected to be useful for testing a wide variety of horse breeds. Thus, in one embodiment, the invention provides a method comprising, in a biological sample obtained or derived from a horse, determining the presence or absence of the LFS-associated deletion, and eliminating horses with the deletion from a breeding stock, or breeding horses which are normal with horses that are carriers or are affected. Thus, the horse breeder/owner can make a selection as to which horses to breed with one another based at least in part on a determination of LFS-associated deletion status.

In one embodiment, the invention provides a method comprising receiving a determination of LFS-associated deletion status (i.e., receiving an identification of one or more horses as normal, carrier, or affected/predisposed to LFS) and selecting a horse or horses for breeding based at least in part on the LFS status of the one or more horse. The status of the LFS deletion can be received in any form or format, such as by electronic mail, by accessing a website that displays the result, which can be hosted anywhere in the world, by telephone, or by paper copy or by receiving the identification in a form recorded in a digital medium.

The following Examples are meant to illustrate but not limit the invention.

Example 1

This Example described the initial mapping of the locus responsible for LFS using a set of 36 horses segregating for LFS. (Analysis of additional horses is set forth in Example 2.) These horses were genotyped using a newly available single nucleotide polymorphism (SNP) chip containing 56,402 discriminatory elements. The whole genome scan identified an associated region containing two functional candidate genes. Exon sequencing of the MYO5A gene from an affected foal revealed a single base deletion in exon 30 that changes the reading frame and introduces a premature stop codon that is described in more detail above. A PCR based Restriction Fragment Length Polymorphism (PCR-RFLP) assay was designed and used to investigate the frequency of the mutant gene. All affected horses tested were homozygous for this mutation. Heterozygous carriers were detected in high frequency in families segregating for this trait, and the frequency of carriers in unrelated Egyptian Arabians was 10.3%. The mapping and discovery of the LFS mutation represents the first successful use of whole genome SNP scanning in the horse for any trait. In order to obtain these and other data described herein, the following materials and methods were used.

Procedures in living animals were limited to the collection of blood by jugular venipuncture or hairs pulled from the mane or tail. Both procedures were conducted according to standard veterinary protocol and inflict minimal, if any pain. All samples were voluntarily submitted by horse owners and/or attending veterinarians according to protocols approved by the Cornell Institutional Animal Care and Use Committee.

Horses. Six initial samples from affected foals plus one foal obtained mid-way through the study, their 31 relatives, as well as 114 individual horses from the general Arabian horse population were available for study. The diagnosis of LFS was made by the attending veterinarian and was consistent with the previously published case reports. Population samples were voluntarily submitted by horse owners from across the US. As multiple samples received from a single owner often included closely related individuals, these horses were selected so that no horse included in the study was related to any other within a single generation. Each of the six affected horses had unique parents, although our analysis showed they were often related farther back in the pedigree. Samples were coded numerically during use to protect the anonymity of participating farms and owners.

Sample Collection and Experimental Strategy. Although LFS is widely-known among breeders of Arabian horses, the number of documented cases available for study and genetic analysis is very low. The six affected foals and their 30 relatives used for SNP genotyping in this Example were collected over a 9 year period from Arabian breeders in various locations in the US. Due to the small number of available affected horses and the smaller than optimal horse SNP chip (only 56K SNPs), we decided to employ a modified family study using all of the available affected foals and their closest relatives, plus extensive pedigrees information available from the Arabian Horse DataSource (Arabian Horse Association, Aurora Colo.).

DNA extraction. Genomic DNA was isolated from fresh or frozen tissue or peripheral blood lymphocytes using the DNeasy Blood and Tissue kit (Qiagen Inc., Valencia, Calif.) following the manufacturer's protocol. DNA was eluted, as well as diluted in, MilliQ (Millipore Corp., Billerica, Mass.) water before use in downstream applications. Hair lysates were prepared for PCR from hair bulbs using standard techniques.

Pedigree Analysis. A pedigree analysis computer program was used to construct a pedigree and calculate $F_i$ statistics as well as the coancestry coefficient for the 36 horses submitted for genotyping in this Example.

EquineSNP50 Genotyping and Analysis. We selected six affected foals, seven of their parents (all those from which samples were available) and 23 close relatives from banked samples. Genotyping on the EquineSNP50 chip was performed by the Genotyping Shared Resource at the Mayo Clinic, (Rochester, Minn.) using 75 µL of approximately 75 ng/µL genomic DNA. Across the 36 samples the genotyping call rate averaged 98% with a minor allele frequency of 0.47, on average. Genotypes were filtered to remove SNPs with a MAF<0.05 and missingness >0.5 using the Plink Whole Genome Analysis Toolset [Purcell S, Neale B, Todd-Brown K, Thomas L, Ferreira Mass., et al. (2007) PLINK: a tool set for whole-genome association and population-based linkage analyses. Am J Hum Genet 81: 559-575.]. A Fisher's exact 3×2 test for a significant genotypic association between each SNP and the affected status was performed using the R statistical package v2.8.1 [R Development Core Team (2008) R: A language and environment for statistical computing. Vienna, Austria: R foundation for Statistical Computing.]. Statistical results were visualized and LD plots generated using Haploview [Barrett J C, Fry B, Maller J, Daly M J (2005) Haploview: analysis and visualization of LD and haplotype maps. Bioinformatics 21: 263-265] or the JMP v7.0 software package (SAS Institute Inc., Cary, N.C.). 281 SNPs from the significantly associated region were phased in to haplotypes using the Phase v2.1.1 [Stephens M, Smith N J, Donnelly P (2001) A new statistical method for haplotype reconstruction from population data. Am J Hum Genet 68: 978-989.]. Genome wide LD was estimated using the $r^2$ statistic in the Plink Whole Genome Analysis Toolset under the following filters: minor allele frequency <0.05 and deviation from Hardy Weinburg Equilibrium p<0.0001. Ten individuals previously genotyped on the EquineSNP50 chip were chosen from the Arabian, Thoroughbred and Saddlebred breeds and compared to ten unrelated founder Egyptian Arabians typed for this study. Values were binned in groups of 5000 and average $r^2$ and inter SNP distance graphed using Excel 2007 (Microsoft Corp., New York, N.Y.).

MYO5A Sequencing. Since no full length mRNA sequence was available for MYO5A in the horse, exons were identified based on homology to the human mRNA sequence (NM_000259) aligned in the UCSC Genome Browser This human transcript, comprising 12,238 nt of mRNA (spanning 114 kb of genomic sequence) encoding 1855 amino acids, is 97.9% identical to the homologous equine sequence. Primers spanning these 39 exons were designed based on the EquCab2.0 genomic sequence from the UCSC Genome Browser using the Primer3 software and purchased from Integrated DNA Technologies (Coralville, Iowa). PCR products were submitted to the Cornell Core Life Sciences Laboratories Center for sequencing using standard ABI chemistry on a 3730 DNA Analyzer (Applied Biosystems Inc., Foster City, Calif.). All sequences were submitted to Genbank under the following accession numbers: GU183550 and GU183551. Sequences were aligned and screened for mutations using the Contig Express program in the Vector NTI Advance v10 suite (Invitrogen Corp., Carlsbad Calif.) or the CodonCode Aligner (CodonCode Corp., Dedham, Mass.). The exon 30 sequence from an LFS horse was translated using Vector NTI Advance v10 and a multiple alignment constructed in Clustal X v.2 using the following amino acid sequences from Genbank: horse XP_001918220.1, human EAW77447.1, mouse CAX15575.1, dog XP_535487.2, cow XP_615219.4, possum XP_001380677.1, chicken CAA77782.1, zebrafish AAI63575.1.

PCR-RFLP Detection. 25 ng of genomic DNA or 24 of hair lysate were amplified by PCR using the following primers: Myo5a.Exon30.RFLP.F 5'-CAG GGC CTT TGA GAA CTT TG-3' (SEQ ID NO:5) and Myo5a.Exon30.R 5'-CAG CCA TGA AAG ATG GGT TT-3' (SEQ ID NO:6). Reactions were assembled in a 10 μL total volume using FastStart Taq DNA Polymerase and included all reagents per the manufacturers recommended conditions (Roche Diagnostics, Indianapolis, Ind.). Thermocycling on an Eppendorf Mastercycler Ep Gradient (Eppendorf Corp., Westbury, N.Y.) was also according to the manufacturer's recommendations with an annealing temperature of 60° C. and a total of 40 cycles for this primer pair. The restriction digest used 10 μL of PCR product, 1.5 units Fau I (New England Biolabs Inc. (NEB), Ipswitch, Mass.), 1×NEB Buffer 4 and enough MilliQ water to bring the reaction volume to 20 μL. Digests were incubated at 55° C. for 1 hour. The resulting products were combined with loading buffer (Gel Loading Dye (6×), NEB) and separated alongside a size standard (100 bp DNA Ladder, NEB) by electrophoresis following standard conditions on a 3% agarose gel (Omnipur Agarose, EMD Chemicals Inc, Gibbstown, N.J.). Agarose gels were stained (SYBRsafe DNA gel stain (10,000×) concentrate, Invitrogen Molecular Probes, Eugene, Oreg.) and visualized under UV illumination (FluroChem HD2, Alpha Innotec Corp., San Leandro Calif.).

Using the foregoing materials and methods, the following results were obtained.

Pedigree Analysis. Pedigree data from the six affected foals available at the time of genotyping supported a recessive mode of inheritance. A single common ancestor was identified six to eight generations from these six affected foals. This common ancestor is present on both sides of the pedigree in each foal. This stallion may represent a founder among this group and this convergence in the pedigree supports identity by descent for the LFS mutation. Average inbreeding ($F_i$) was 0.0861 for affected foals, versus 0.0394 for parents of foals. The extended pedigree also allowed for the calculation of the coancestry coefficient between each living relative and the nearest affected foal in the pedigree. Based on this calculation we predicted that the frequency of the LFS allele would be 0.42 among the 30 relatives used for genotyping.

Association Mapping. Genotypic association tests using the six affected foals and their 30 healthy relatives revealed a single region on chromosome 1 (ECA1) with statistical significance above that of the rest of the genome. These 14 highly significant SNPs encompassed a region spanning 10.5 Mb (ECA1:129228091 to 139718117). Although extensive inbreeding and relatedness between affected individuals produced a high number of coincidentally significant ($p<0.05$) SNPs across the genome, the high peak significance of SNPs in the candidate region ($p=4.62e-6$) was convincing evidence for association. In total there were 14 SNPs at this locus that were more significantly associated with the LFS trait than any other region in the genome. The twelve LFS bearing chromosomes from the six affected horses represented only four unique haplotypes for this 10 Mb candidate region. These four haplotypes possessed one large block of 27 SNPs in common. This 1.6 Mb region was homozygous in all six affected horses and heterozygous in obligate carriers as well as many of the living relatives, as was predicted by the coancestry in the pedigree. The linkage disequilibrium (LD) structure and p-values in this likely location for a recessive mutation were plotted (data not shown) and we determined that only 10 Ensembl Gene Predictions fell within this region, including MYO5A, but not RAB27A.

Population Structure. Genome-wide observed homozygosity from the genotypes obtained using the EquineSNP50 chip was on average 65.14%. This was much higher than expected considering the homozygosity of the inbred mare chosen for whole genome sequencing was estimated at only 46%. The ten founder Egyptian Arabian individuals from this study, as well as an additional 10 unrelated individuals from the Thoroughbred, Arabian (non-Egyptian) and Saddlebred breeds were used to calculate average genome-wide LD. This calculation revealed that the length of LD in the Egyptian was similar to that of the Thoroughbred, a breed with a long history of a closed studbook and relatively small foundation population. LD in the Egyptian was also much longer than that of the Arabian population as a whole, which was most similar to the Saddlebred. The Saddlebred breed registry was closed in 1917 and derived from fairly diverse types of horse suitable for use as transportation under saddle and in harness.

Candidate Gene Sequencing. Individual PCR amplification and sequencing of the 39 exons of MYO5A from a LFS affected foal revealed three SNPs and one polymorphic microsatellite in intronic sequence, as well as a single base deletion in exon 30 of MYO5A (Table 1).

TABLE 1

| HGVS Nomenclature | Within Gene Location | Type |
| --- | --- | --- |
| g.138148824A > G | Intron 3 +100 | SNP |
| g.138168098G > A | Intron 6 +189 | SNP |
| g.138230294C > T | Intron 27 −156 | SNP |
| g.138235715del[a] | Exon 30 +148 | Frameshift |
| g.138253441GT(10_12) | Intron 35 −79 | (GT) satellite |

([a]LFS associated polymorphism)

This deletion was further confirmed by sequencing in a second foal and its heterozygous parents. The deletion is termed ECA1 g.138235715del per Human Genome Variation Society (http://www.hgvs.org/mutnomen/) nomenclature. This deletion changes the reading frame, creating a premature stop codon in the translation of exon 30, 12 amino acids following the mutation. A multiple alignment of the predicted LFS exon 30 amino acid sequence, as well as the wild type sequence from eight species, shows that this region of the myosin Va protein is highly conserved. The four intronic polymorphisms were not predicted to change the function of myosin Va and were therefore not investigated further.

Association and Frequency Estimates. We designed a PCR-RFLP assay using the Fau I restriction enzyme to detect this deletion (FIG. 1). Digestion of the PCR product produces a positive control fragment of 289 bp in all genotypes. The positive control is a second digestion site that is common to all horses, irrespective of LFS status. Presence of the deletion abolishes a Fau I site, changing the normal pattern of a 386 bp and a 90 bp fragment in to a single 476 bp product. All seven affected foals (the six originally submitted for mapping plus one additional obtained after mapping was completed) were homozygous for the deletion (Table 2).

TABLE 2

| Genotypes[a] | +/+ | +/− | −/− |
|---|---|---|---|
| Affected (Homozygotes) | 0 | 0 | 7 |
| Parents (Carriers) | 0 | 8 | 0 |
| Other Relatives (Unknown Genotype) | 7 | 16 | 0 |
| Total | 7 | 24 | 7 |

([a]"+" stands for the wild type while "−" indicates the deletion)

Eight out of the 14 parents of these affected foals were available for sampling and all carried the deletion. Among 23 relatives of affected foals 16 were identified as carriers of the deletion. A sample group of 114 Arabian horses was tested to provide a rough estimate of the frequency of the MYO5A exon 30 deletion, and therefore Lavender Foal Syndrome, in the breed as a whole (Table 3). 10.3% of Egyptian Arabians (six out of 58 horses) and 1.8% of non-Egyptian Arabians (one out of 56 horses) were identified as carriers.

TABLE 3

| Genotypes[a] | +/+ | +/− | −/− | LFS Allele Freq. |
|---|---|---|---|---|
| Egyptian Arabian | 52 | 6 | 0 | 0.052 |
| Other Arabian | 55 | 1 | 0 | 0.0089 |
| Total | 107 | 7 | 0 | 0.031 |

([a]"+" stands for the wild type while "−" indicates the deletion)

Example 2

In Example 1 it is shown that a single base pair deletion in the MYO5A gene is likely responsible for LFS. Here we show an analysis of different Arabian horse breeds and provide a rationale for the usefulness of the invention in other horse breeds which may also be at risk for propagating the LFS-associated allele. In particular, within the Arabian breed are several sub-groups or sub-breeds of Arabian horses, traditionally defined by the geographic region in which they are located. Examples of these sub-groups include Australian, Polish, and Russian Arabians. From previous literature and case studies, LFS has to date only been clinically observed in the Egyptian Arabian. However, because all of these sub-groups have common ancestries, the LFS mutation may be found across the breed and in other breeds if the mutation occurred prior to the export of horses from the Arabian deserts. Additionally, the Arabian horse has contributed to the development of many other breeds including, the Thoroughbred, Standardbred, Morgan, Quarter Horse, and Percheron. Therefore it is possible the LFS allele could be found in these breeds as well. Table 4 summarizes results of an embodiment of the LFS test performed on different breeds and sub-breeds. LFS carriers are denoted by +/−, and −/− denotes a horse that does not carry the LFS allele.

TABLE 4

| Breed | +/− | −/− | Total |
|---|---|---|---|
| Spanish-Egyptian Arabian | 0 | 47 | 47 |
| German Arabian | 7 | 161 | 168 |
| Thoroughbred | 0 | 78 | 78 |
| Standardbred | 0 | 30 | 30 |

To obtain the data presented in Table 4, DNA samples were collected from 78 Thoroughbreds, 30 Standardbreds, 47 Spanish-Egyptian Arabians, and 168 German Arabians, all of which were verified to be unrelated to one another within one generation. Genotypes for LFS were determined using the PCR-RFLP assay described in Example 1. Of the 78 Thoroughbred samples, 30 Standardbreds, and 47 Spanish-Egyptian Arabians, there were no LFS carriers found. Of the 168 German Arabians genotyped seven were heterozygous for the MYO5A deletion, and were deemed LFS carriers. Pedigree analysis for several of the German Arabian carriers revealed highly inbred bloodlines tracing back to common founders previously identified in the pedigrees of carriers. As can be seen from Table 4, it appears that LFS is found primarily in the Arabian horse, specifically those individuals tracing back to Egyptian bloodlines. Our data also suggests that the LFS mutation probably arose after the creation of other horse breeds such as the Thoroughbred and Standardbred. Shifts in the breeding paradigm of the domestic horse may have contributed to the emergence of recessive deleterious mutations in some breeds. However, in a similar fashion to the domestic dog, horses have begun to change roles in society and culture, from use in transportation and agriculture, to that of a companion animal. While some sport horse breeds maintain selection based on quantitative ability, others are now valued highly for having a rare or popular pedigrees. Cautious strategies to avoid excessive inbreeding and maintain genetic diversity may be needed to avoid an increase of genetic disease in these breeds of horse, and the present invention provides one such strategy. Furthermore, as more and more interbreeding of horse types becomes popular, there will remain an ongoing need for the present invention to screen different types of breeds of horses for the LFS deletion.

It will be apparent from the foregoing that we describe here the first successful use of the EquineSNP50 genotyping platform in identification of the mutation responsible for a genetic disorder in the horse. We have described a frameshift mutation in the MYO5A gene that leads to Lavender Foal Syndrome in the horse. This task was made more challenging by the small number (six) of DNA samples from available affected foals (an analysis that is expanded as set forth in Example 2). We combined our strategy with analysis of pedigree data to select control samples from the extended family and by utilizing a genotype association rather than allelic association statistic in combination with identification of regions of homozygosity. The extreme predicted impact on function resulting from the single base deletion in MYO5A exon 30 makes it a logical cause of LFS. Indeed, an alignment of MYO5A exon 30 amino acid sequences from 8 diverse species shows that the exon is completely conserved in horses, humans, mice, dogs and cattle and contains only a few changes in the possum, chicken, and zebrafish. Our newly discovered deletion in exon 30 of MYO5A leads to a frame shift and premature termination of transcription. Loss of the 379 amino acids at the C-terminus of the protein, which encode a portion of the secretory vesicle-specific binding domains of the globular tail, would likely impair binding of myosin Va to those cargo organelles bearing the appropriate receptors [Pashkova N, Catlett N L, Novak J L, Wu G, Lu R, et al. (2005) Myosin V attachment to cargo requires the tight association of two functional subdomains. J Cell Biol 168: 359-364.]. Additionally, the quantity of MYO5A protein may be significantly reduced, as is often observed in experimentally truncated constructs of this gene [Au J S, Huang J D (2002) A tissue-specific exon of myosin Va is responsible for selective cargo binding in melanocytes. Cell Motil Cytoskeleton 53: 89-102.]. The resulting loss of vesicle traffic could be expected to interfere with the normal function of melanocytes and neurons. The neurologic deficits exhibited by LFS affected foals are relatively more severe than the symptoms reported in human cases of Griscelli Syndrome, which are most often due to changes in a single amino acid rather than loss of a significant portion of the transcript [Sanal O, Ersoy F, Tezcan I, Metin A, Yel L, et al. (2002) Griscelli disease: genotype-phenotype correlation in an array of clinical heterogeneity. J Clin Immunol 22: 237-243.]. However, in the mouse a broad spectrum of phenotypes are observed, owing to the variety of causative mutations available for study. It should be noted that, in arriving at the present invention, we identified a conserved block of 1.6 Mb in common in the four LFS bearing haplotypes. This is smaller than would be expected considering the average rate of decay of LD across just the six to eight generations that separate these four haplotypes. Indeed, upon further research of the pedigrees from carriers identified during screening for the LFS allele in our sample of 107 Arabian horses, we identified carriers who did not possess this candidate founder in their pedigree. Therefore it is likely the true founder of this mutation occurred far earlier.

While the invention has been described through illustrative examples, routine modifications will be apparent to those skilled in the art, which modifications are intended to be within the scope of the invention.

We claim:

1. A method for determining whether or not a biological sample comprises a mutation, the method comprising amplifying nucleic acids from the biological sample by polymerase chain reaction (PCR) to obtain amplified nucleic acids, subjecting the amplified nucleic acids to restriction endonuclease digestion to obtain restriction digest fragments of the amplified nucleic acids, and analyzing the restriction digest fragments to determine the presence or absence of a single nucleotide deletion which introduces a translational stop codon in the 49th codon of exon 30 of the equine MYO5A gene, thereby determining whether the deletion is present: i) in both copies of the exon 30 of the equine MYO5A gene, thereby determining homozygosity for the deletion; or ii) in only one copy of the exon 30 of the equine MYO5A gene, thereby determining heterozygosity for the deletion; or iii) in neither copy of the exon 30 of the equine MYO5A gene, thereby determining homozygosity for absence of the deletion.

2. The method of claim 1, wherein the analyzing comprises determining homozygosity for a sequence comprising SEQ ID NO:1.

3. The method of claim 1, wherein the analyzing comprises determining SEQ ID NO:1 and SEQ ID NO:2.

4. The method of claim 1, wherein the analyzing comprises determining homozygosity for SEQ ID NO:2.

5. The method of claim 1, wherein the endonuclease digestion is performed using a Fau I restriction endonuclease.

6. The method of claim 1, wherein the amplifying nucleic acids from the sample by the PCR is performed using at least one primer comprising the sequence of SEQ ID NO:5 or SEQ ID NO:6.

7. A method for determining that a sample comprising nucleic acids does not contain a normal equine MYO5A gene by amplifying nucleic acids from the sample by polymerase chain reaction (PCR) to obtain amplified nucleic acids, subjecting the amplified nucleic acids to restriction endonuclease digestion to obtain restriction digest fragments of the amplified nucleic acids, and analyzing the restriction digest fragments to determine the presence of a single nucleotide deletion which introduces a translational stop codon in the 49th codon of exon 30 of the equine MYO5A gene.

8. The method of claim 7, wherein the analyzing comprises determining the sequence of SEQ ID NO:2.

9. The method of claim 7, wherein the endonuclease digestion is performed using a Fau I restriction endonuclease.

10. The method of claim 7, wherein the amplifying nucleic acids from the sample by the PCR is performed using at least one primer comprising the sequence of SEQ ID NO:5 or SEQ ID NO:6.

* * * * *

SEQUENCE LISTING

```
<160> NUMBER OF SEQ ID NOS: 6

<210> SEQ ID NO 1
<211> LENGTH: 201
<212> TYPE: DNA
<213> ORGANISM: Horse

<400> SEQUENCE: 1
ggctcctgga atcccagctc cagtcgcaga agaggagcca tgagaatgag gctgaagccc      60
tccgcgggga gatccagagc ctgaaggagg agaacaaccg gcagcagcag ctgctggccc     120
agaacctgca gctgccccca gaggcccgca tcgaggccag cctgcagcat gagatcaccc     180
ggctgaccaa cgaaaacttg g                                               201

<210> SEQ ID NO 2
<211> LENGTH: 200
<212> TYPE: DNA
<213> ORGANISM: Horse

<400> SEQUENCE: 2
ggctcctgga atcccagctc cagtcgcaga agaggagcca tgagaatgag gctgaagccc      60
tccgcgggga gatccagagc ctgaaggagg agaacaaccg gcagcagcag ctgctggccc     120
agaacctgca gctgccccca gaggccgcat cgaggccagc ctgcagcatg agatcacccg     180
gctgaccaac gaaaacttgg                                                 200

<210> SEQ ID NO 3
<211> LENGTH: 66
<212> TYPE: PRT
<213> ORGANISM: Horse

<400> SEQUENCE: 3

Leu Leu Glu Ser Gln Leu Gln Ser Gln Lys Arg Ser His Glu Asn Glu
1               5                   10                  15

Ala Glu Ala Leu Arg Gly Glu Ile Gln Ser Leu Lys Glu Glu Asn Asn
            20                  25                  30

Arg Gln Gln Gln Leu Leu Ala Gln Asn Leu Gln Leu Pro Pro Glu Ala
        35                  40                  45

Arg Ile Glu Ala Ser Leu Gln His Glu Ile Thr Arg Leu Thr Asn Glu
    50                  55                  60

Asn Leu
65

<210> SEQ ID NO 4
<211> LENGTH: 60
<212> TYPE: PRT
<213> ORGANISM: Horse
```

```
<400> SEQUENCE: 4

Leu Leu Glu Ser Gln Leu Gln Ser Gln Lys Arg Ser His Glu Asn Glu
1               5                   10                  15

Ala Glu Ala Leu Arg Gly Glu Ile Gln Ser Leu Lys Glu Glu Asn Asn
                20                  25                  30

Arg Gln Gln Gln Leu Leu Ala Gln Asn Leu Gln Leu Pro Pro Glu Ala
            35                  40                  45

Ala Ser Arg Pro Ala Cys Ser Met Arg Ser Pro Gly
        50                  55                  60

<210> SEQ ID NO 5
<211> LENGTH: 20
<212> TYPE: DNA
<213> ORGANISM: Artificial sequence
<220> FEATURE:
<223> OTHER INFORMATION: Forward primer for exon amplification

<400> SEQUENCE: 5
cagggccttt gagaactttg                                           20

<210> SEQ ID NO 6
<211> LENGTH: 20
<212> TYPE: DNA
<213> ORGANISM: Artificial Sequence
<220> FEATURE:
<223> OTHER INFORMATION: Reverse priimer for exon amplification

<400> SEQUENCE: 6
cagccatgaa agatgggttt                                           20
```